(12) United States Patent
Domeika et al.

(10) Patent No.: US 10,610,130 B2
(45) Date of Patent: Apr. 7, 2020

(54) MEASURING LIMB RANGE OF MOTION

(71) Applicant: Intel Corporation, Santa Clara, CA (US)

(72) Inventors: Maximillian Domeika, Sherwood, OR (US); Eliran Dror, Maale Adumim (IL); Ned Smith, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 90 days.

(21) Appl. No.: 16/023,011

(22) Filed: Jun. 29, 2018

(65) Prior Publication Data
US 2019/0038181 A1  Feb. 7, 2019

(51) Int. Cl.
*A61B 5/107* (2006.01)
*G16H 30/40* (2018.01)
*A61B 5/11* (2006.01)
*A61B 5/00* (2006.01)

(52) U.S. Cl.
CPC .......... *A61B 5/1075* (2013.01); *A61B 5/0064* (2013.01); *A61B 5/1071* (2013.01); *A61B 5/1072* (2013.01); *A61B 5/1074* (2013.01); *A61B 5/1079* (2013.01); *A61B 5/1121* (2013.01); *A61B 5/1128* (2013.01); *A61B 5/7267* (2013.01); *G16H 30/40* (2018.01); *A61B 2560/0223* (2013.01)

(58) Field of Classification Search
CPC ... A61B 5/0064; A61B 5/1072; A61B 5/1075; A61B 5/1079; A61B 5/1121; A61B 5/1128; A61B 5/7267; G16H 30/40
See application file for complete search history.

(56) References Cited

U.S. PATENT DOCUMENTS

2017/0360578 A1 * 12/2017 Shin ................ G09B 23/286
2019/0213389 A1 *  7/2019 Peruch ............. G06K 9/00201

OTHER PUBLICATIONS

Chi et al., "Body scanning of dynamic posture", International Journal of Clothing Science and Technology, 2006, vol. 18 Issue: 3, Abstract, 3 pages.
Choi et al., "3D body scan analysis of dimensional change in lower body measurements for active body positions," Textile Research Journal, Aug. 13, 2010, Abstract, 3 pages.
"Temporal-3dMD Systems (4D)", retrieved from 3dmd.com/3dmd-systems/dynamic-surface-motion-capture-4d/, retrieved on Jun. 26, 2018, 16 pages.
"Body+Measure+Scan+AI=Bodylabs delicacy", retrieved from youtube.com/watch?v=VCgNxhWh-2U, Jul. 29, 2016.

* cited by examiner

*Primary Examiner* — David Bilodeau
(74) *Attorney, Agent, or Firm* — Jordan IP Law, LLC (57) ABSTRACT

A system, method, and computer readable medium for measuring limb range of motion. The method includes initializing a scanning area. A classifier trained to recognize limbs is loaded into memory. A frame representing a 3D point cloud having at least one limb of a person in motion is captured. A box fitting algorithm is performed on the captured at least one limb to enable the classifier to identify the at least one limb. One or more boxes generated from the box fitting algorithm are sliced into a plurality of 2D point clouds to measure and record the circumference of each 2D point cloud to obtain limb range of motion parameters. The limb range of motion parameters are a maximum and a minimum size of the at least one limb as a function of soft tissue expansion and contraction of the limb while under pressure, force, and/or motion.

25 Claims, 9 Drawing Sheets

| Measurement | Current at t | Maximum | Minimum | Average |
|---|---|---|---|---|
| Foot length | 25.4cm | 25.8cm | 25.1cm | 25.6cm |
| Foot width | 14.2cm | 15.0cm | 14.0cm | 14.7cm |
| Foot girth | 23.0cm | 23.2cm | 23.0cm | 23.1cm |
| Calf Circumference | 32.1cm | 32.1cm | 31.0cm | 31.8cm |
| Toe Angle | 140 | 180 | 95 | 160 |

Logic 704

MEASURING LIMB RANGE OF MOTION

TECHNICAL FIELD

Embodiments generally relate to measuring limbs. More particularly, embodiments relate to measuring limb dimensions of a person while in motion to facilitate more accurate fitting information between customer, manufacturer and retailer.

BACKGROUND

One of the challenges of online shopping is the cost of incorrect sizes. According to research by Fits.me, one (1) in four (4) apparel items bought online are returned and 70% of the time it is due to the apparel item being an incorrect size for the customer.

Regular 2D cameras have been employed previously to create depth representations of an individual for determining fitting information. Such solutions employing the depth cameras analyzed only one static point representation of a limb of an individual. Some 3D camera based solutions enable real time capture of depth information from multiple body parts to ascertain articulation data or anatomical data. Many of these methods focus on fit of clothing on simulated soft tissue. They do not measure limb range of motion for optimization of apparel creation and fitting.

BRIEF DESCRIPTION OF THE DRAWINGS

The various advantages of the embodiments will become apparent to one skilled in the art by reading the following specification and appended claims, and by referencing the following drawings, in which:

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

DESCRIPTION OF EMBODIMENTS

Technology to create an in motion 3-D representation of one or more limb(s) is provided. Embodiments include a measurement device consisting of one or more depth cameras that together have a 360-degree view of the limb in motion. In one embodiment, a single depth camera may be used that rotates around the limb in motion. In another embodiment, multiple depth cameras may be employed, with each depth camera statically placed to encircle the limb in motion. The measurement device is connected to a computer system to allow the capture and analysis of in-motion 3-D representations of one or more limb(s) to enable the manufacture of apparel based upon flex positions of the customers. Actual changes in limb sizes as a result of muscular expansion and contraction are obtained through real time depth measurements. These changes in limb sizes over a cycle of an activity of motion performed by a particular subject (i.e., person) represent a data set that encompasses the full range of shape changes of the limb. By obtaining measurements of the subject's limb while in a static position as well as while moving dynamically, manufacturers may use the data set (full range of dimensions of the limb) to create better fitting apparel, enabling customers to purchase the apparel from online retailers with a high probability of success that the apparel will fit properly.

The depth cameras create an in-motion 3D representation of the limb, recording information such as, for example, size, shape, and circumference of the limb. As a person is moving, the very act of motion changes the dimensions of the limb due to muscular expansion/contraction and pressure from the outside environment, such as, for example, the ground. Machine learning techniques are used to identify the limbs and to map previously learned motions of a sample of customers onto a new input data set. Classifier files, box fitting, and slicing techniques are used to obtain maximum and minimum dimensions of the limb. The system records maximum, minimum and average dimensions of the limb as a function of soft tissue expansion and contraction under pressure, force and/or motion. The maximum and minimum data provide range of motion measurements that are useful for both creating apparel and fitting apparel. For example, recording the maximum and minimum calf circumference of a large sample of customers enables manufacturers to create different boots sizes using materials and fabric types that are optimized for those customers. Once manufacturers have incorporated this data into their manufacturing process, they can publish the recommended maximum and minimum calf circumference for different boot sizes and can match them against a specific customer's measurements during the fitting process.

Embodiments also create a joint model for the limb which includes range of motion information. The system measures joint range and axis of rotation, achieving a full spectrum of range and motion analysis due to inferencing techniques given a simple sample of range and position inputs. For example, if shoe manufacturers know the range of motion of toe joints across a large sample of their customers, they may optimize the location and degree of flexibility of a shoe's sole.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device). As used herein, the term "logic" and "module" may refer to, be part of, or include an application specific integrated circuit (ASIC), an electronic circuit, a processor (shared, dedicated, or group), and/or memory (shared, dedicated, or group) that execute one or more software or firmware programs having machine instructions (generated from an assembler and/or a compiler), a combinational logic circuit, and/or other suitable components that provide the described functionality.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, it may not be included or may be combined with other features.

Figure 1:
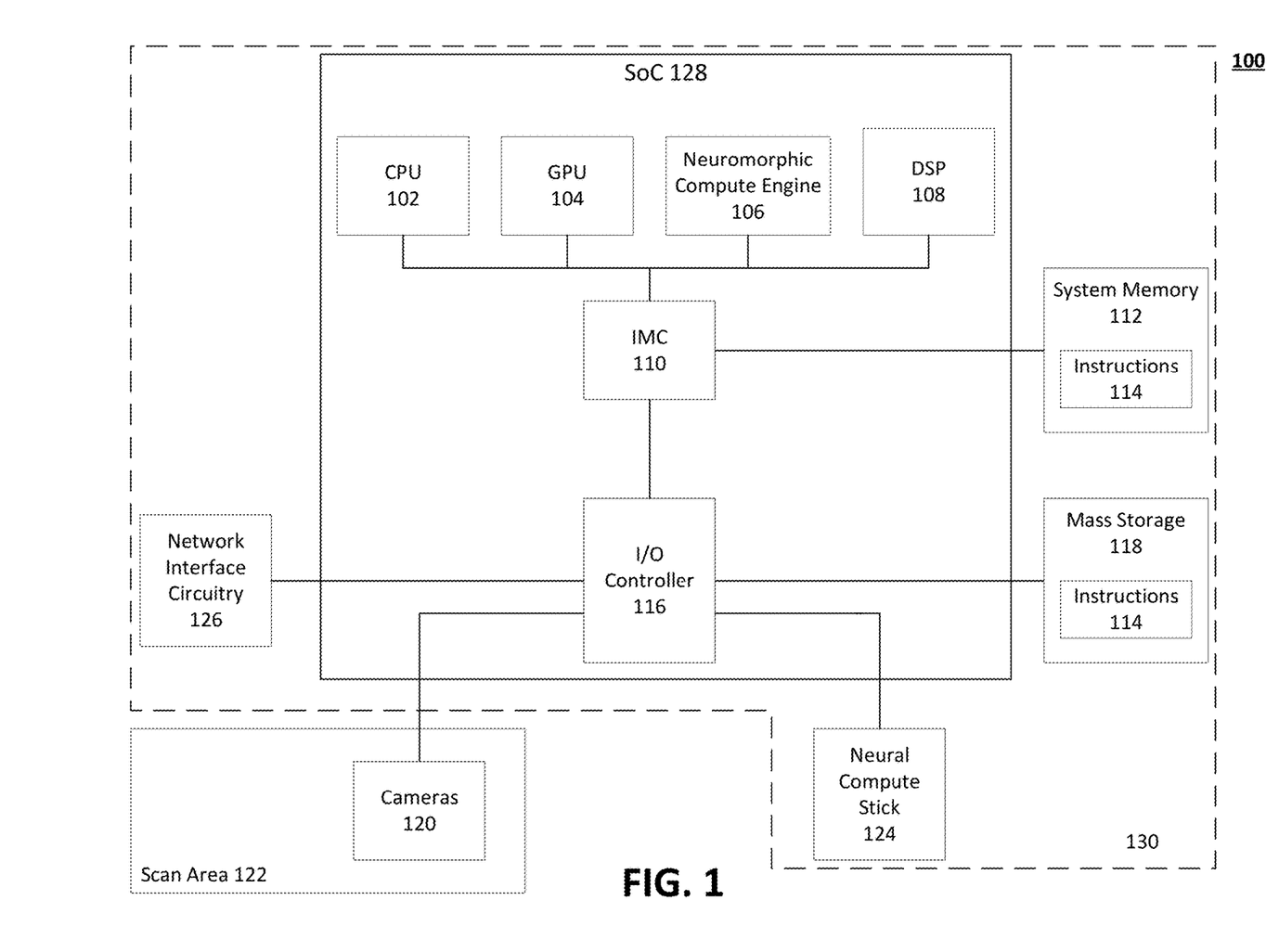
FIG. 1 is a block diagram of an example of a limb range of motion measurement system according to an embodiment.

FIG. 1 is a block diagram of an example of a limb range of motion measurement system 100 according to an embodiment. As previously indicated, system 100 includes a measurement device comprising one or more 3-D cameras 120 located within a scanning area 122, and coupled to a computer system 130. The one or more 3-D cameras have a 360-degree view of a limb in motion. In one embodiment, a single 3-D camera capable of rotating around the limb in motion may be used. In another embodiment, multiple 3-D cameras may be used, with each 3-D camera statically placed to encircle the limb in motion. In one embodiment, the 3-D cameras may be, for example, Intel® RealSense™ depth cameras.

The computer system 130 includes multiprocessors such as a first processor 102 (e.g., host processor, central processing unit/CPU) and a second processor 104 (e.g., graphics processing unit/GPU). The first processor or CPU 102 is the central or main processor for carrying out instructions of computer programs, such as, for example, a method for measuring limb range of motion. The second processor or GPU 104 is primarily used to render 3D graphics, such as, for example, a 3-D graphic of a limb of a person being measured. The GPU 104 may also be utilized to assist the CPU 102 in non-graphics computations. The CPU 102 and/or the GPU 104 may include a core region with one or several processor cores (not shown).

The computer system 130 also includes multiple compute engines to provide artificial machine intelligence. The compute engines include a neuromorphic compute engine 106 and a DSP (Digital Signal Processor) 108. The neuromorphic compute engine 106 is a hardware based accelerator used to increase the performance of deep neural networks. The neuromorphic compute engine 106 may be used to run neural networks, such as, for example, a convolutional neural network used to enhance the collected data samples. The DSP 108 is an on-chip hardware block designed to run deep neural networks at high speed and low power without compromising accuracy. The DSP 108 may be used to accelerate deep learning inferences at the edge. Thus, the DSP 108 may be used for machine learning to train a classifier to recognize the types of limbs captured by the one or more 3D camera(s) 120.

The CPU 102, GPU 104, and the compute engines 106 and 108 are communicatively coupled to an integrated memory controller (IMC) 110. The IMC 110 is coupled to a system memory 112 (volatile memory, 3D XPoint memory). The CPU 102, GPU 104, and the compute engines 106 and 108 may also be coupled to an input/output (I/O) module 116 that communicates with mass storage 118 (e.g., non-volatile memory/NVM, hard disk drive/HDD, optical disk, solid state disk/SSD, flash memory), the one or more 3D cameras 120 (housed within the scanning area 122 to obtain in-motion limb measurements), one or more neural compute sticks (NCS) 124, such as, for example, the Intel® Movidius™ NCS (a USB-based deep learning/self-contained device used for artificial intelligence (AI) programming at the edge), and network interface circuitry 126 (e.g., network controller, network interface card/NIC).

The one or more NCS(s) 124 may provide dedicated deep neural network capabilities to the multiprocessors (102 and 104) and the compute engines (106 and 108) at the edge. Each of the one or more NCS(s) 124 include a VPU (Vision Processing Unit) to run real-time deep neural networks directly from the device to deliver dedicated high performance processing in a small form factor. In embodiments, the one or more NCS(s) may be used to perform pattern matching based on the classifier trained to recognize limbs.

The network interface circuitry 126 may provide off platform communication functionality for a wide variety of purposes, such as, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications, 4G LTE (Fourth Generation Long Term Evolution), Bluetooth, WiMax (e.g., IEEE 802.16-2004, LAN/MAN Broadband Wireless LANS), Global Positioning System (GPS), spread spectrum (e.g., 900 MHz), and other radio frequency (RF) telephony purposes. Other standards and/or technologies may also be implemented in the network interface circuitry 126.

The network interface circuitry 126 may therefore enable the exchange of measurement information with customers, manufacturers, retailers, etc. The network interface circuitry 126 may also enable communication with various cloud services to construct and maintain personal profile records of limb measurements, purchase history and personal closet inventory tracking that establishes a useful lifetime of an item for a customer throughout the item's lifecycle.

Although the CPU 102, the GPU 104, the compute engines 106 and 108, the IMC 110, and the I/O controller 116 are illustrated as separate blocks, these components may be implemented as a system on chip (SoC) 128 on the same semiconductor die.

Figure 3:
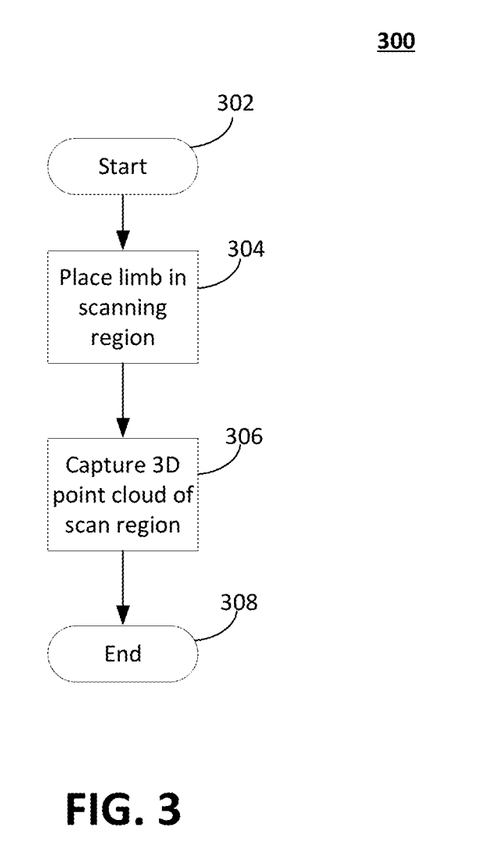
FIG. 3 is a flow diagram of an example method of obtaining a 3D point cloud according to an embodiment.
Figure 4:
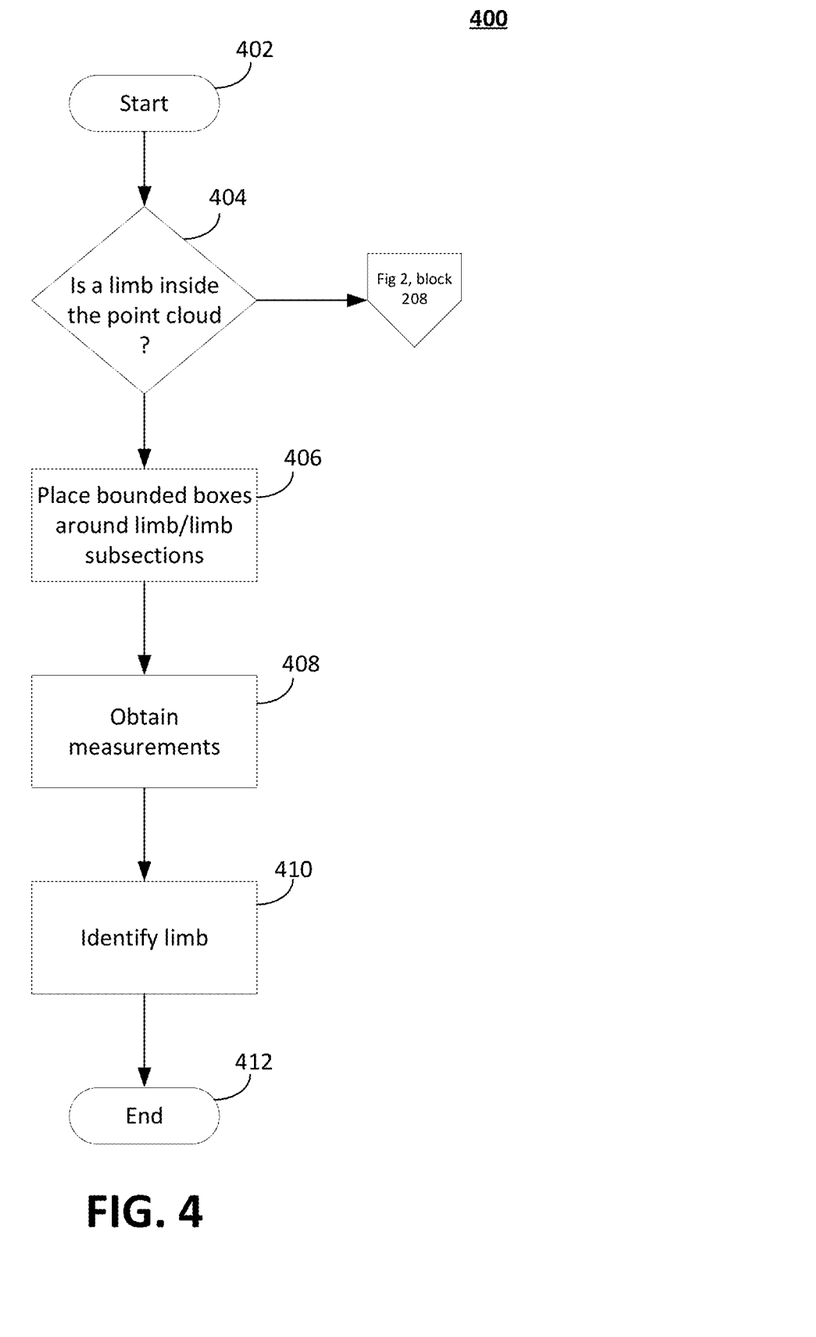
FIG. 4 is a flow diagram of an example method of box fitting a limb within a 3D point cloud image according to an embodiment.

The system memory 112 and/or the mass memory 118 may be memory devices that store instructions 114, which when executed by the processors 102 and/or 104 or the compute engines 106 and/or 108, cause the system 100 to perform one or more aspects of methods 200, 300, and 400 for measuring limb range of motion, described below with reference to FIGS. 2, 3, and 4. Thus, execution of the instructions 114 may cause the system 100 to capture limb range of motion measurements using the one or more 3-D camera(s) 120.

Limb range of motion measurements of a user may be performed in the scanning area 122 (not drawn to scale). The scanning area may be large enough for the user to perform movements (i.e., activities) that enable changes in limb size as a result of muscular expansion and contraction while being captured by the one or more 3-D cameras 120. Such movements may include, for example, walking, jogging, running, jumping, hopping, skipping, flexing legs, arms, lower and upper body, etc. Based on the activity being performed by the user, the limb range of motion measurements may vary. For example, one's calf may expand and contract more when a person is running or jogging versus when a person is walking.

Figure 2:
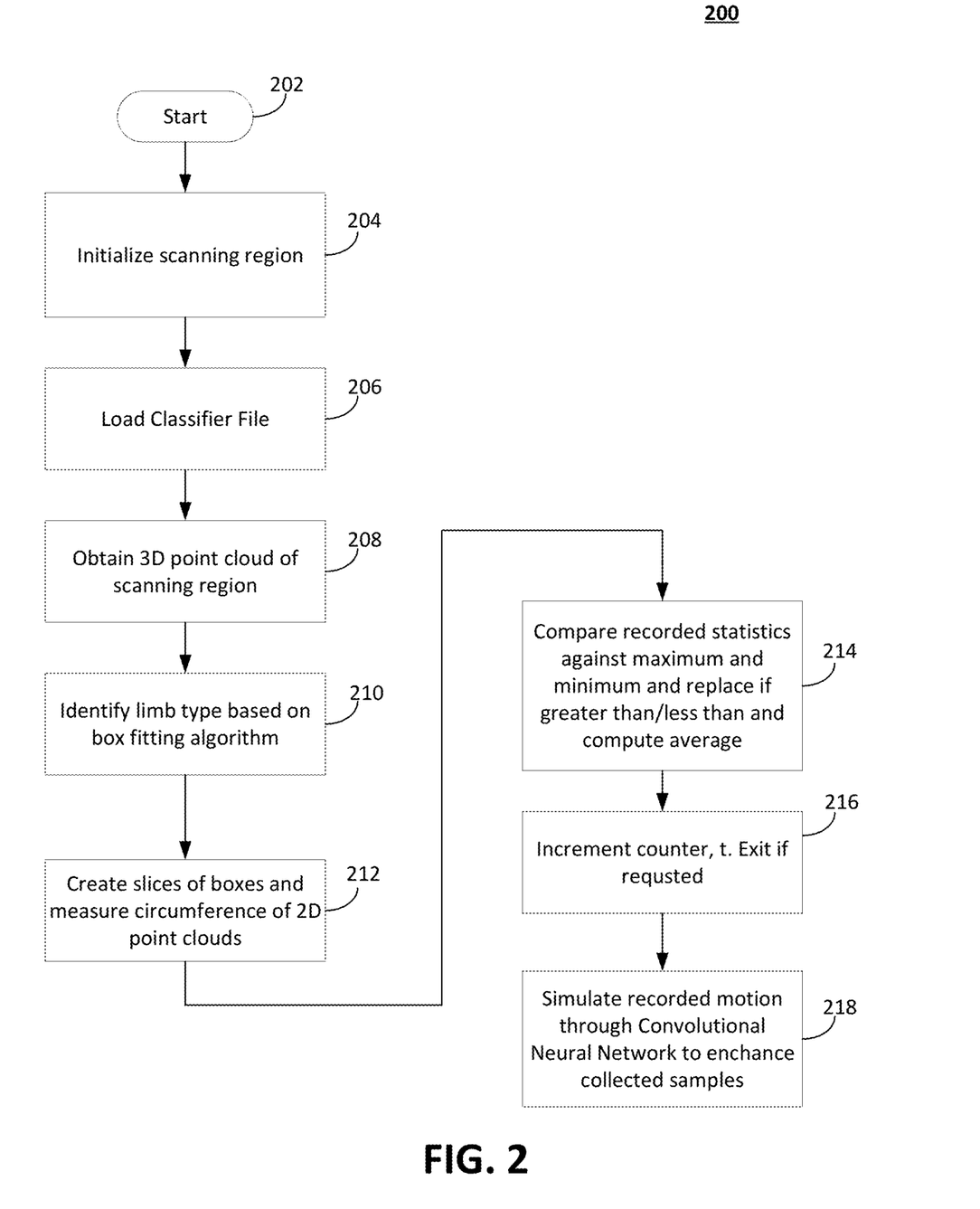
FIG. 2 is a flow diagram of an example method of measuring limb range of motion according to an embodiment.

FIG. 2 is a flow diagram of an example method 200 of measuring limb range of motion according to an embodiment. The method 200 may generally be implemented in a system such as, for example, the limb measurement system 100 as shown in FIG. 1. More particularly, the method 200 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), and fixed-functionality logic hardware using circuit technology such as, for example, application specific integrated circuit (ASIC), complementary metal oxide semiconductor (CMOS) or transistor-transistor logic (TTL) technology, or any combination thereof.

For example, computer program code to carry out operations shown in the method 200 may be written in any combination of one or more programming languages, including an object-oriented programming language such as JAVA, SMALLTALK, C++ or the like and conventional procedural programming languages, such as the "C" programming language or similar programming languages. Additionally, logic instructions might include assembler instruction, instruction set architecture (ISA) instructions, machine instruction, machine dependant instruction, microcode, state setting data, configuration data for integrated circuitry, state information that personalizes electronic circuitry and/or other structural components that are native to hardware (e.g., host processor, central processing unit (CPU), microcontroller, etc.).

The process begins in block 202, where the process immediately proceeds to block 204. In block 204, a scanning area is initialized. The system calibrates a 3-dimensional scanning region (i.e., x, y, z) relative to the walls and floor of the scanning area covered by the 3D camera mechanism. Human limbs or any other objects are not allowed in the scanning region during calibration. The process then proceeds to block 206.

In block 206, a classifier file is loaded into the system. The system initializes a classifier that has been trained to recognize human limbs based upon a box fitting approach. Each portion of a limb has a geometry. The box fitting approach (also referred to as the bounding box approach) places rectangular boxes of different sizes around a limb or portion of a limb. The classifier is trained to recognize box fitted human limbs within a point cloud based on the size of the box(es) placed around the limb or portions of the limb. By training on different box sizes, the classifier may distinguish between a forearm, wrist, hand, leg, shoulder, etc. captured by the one or more 3D cameras 120 discussed above with reference to FIG. 1. In one embodiment, the classifier may be trained using the DSP 108. The classifier may be trained using a variety and/or combination of techniques, such as, for example, Logistic Regression, Ordinary Least Squares, Linear Regression, Naïve Bayes Classifier, Bayesian Network, K-means Clustering, Random Forest, Principal component Analysis, K-nearest neighbors, Decision tree learning, Multivariate Adaptive Regression, Support vector machine, Linear discriminant analysis, and others. In one embodiment, a method of training the classifier may employ a Convolutional Neural Network (CNN). Training sets of multiple images of human limbs with correct identification and expected joints and appendages are provided as input into the CNN, which may run on the neuromorphic compute engine 106. The training sets may be generated ahead of time and are continuously updated each time a new user is measured. In one embodiment, the training sets may be generated manually. The classifier provides a method of identifying the limbs to track, their relative sizes, orientation, and connection points. The process proceeds to block 208.

In block 208, a 3D point cloud of the scan region is obtained. FIG. 3 is a flow diagram of an example method 300 of obtaining a 3D point cloud according to an embodiment. The method 300 may generally be implemented in a system such as, for example, the limb measurement system 100 as shown in FIG. 1. More particularly, the method 300 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, and fixed-functionality logic hardware using circuit technology such as, for example, ASIC, CMOS or TTL technology, or any combination thereof.

The process begins in block 302 where the process immediately proceeds to block 304. In block 304 the limb of a person to be measured is fully placed within the scan region. The person to be measured must be wearing tight fitting clothes or the limb must be exposed. In an embodiment, the person may be in motion. For example, the person may be walking, jogging, running, jumping, hopping, flexing, etc. This enables measurements of the limb to be captured when muscles are expanding and contracting. The process then proceeds to block 306.

In block 306, a 3D point cloud of the scan region is obtained using the one or more 3D cameras 120 during a time interval. The one or more 3D cameras 120 collect a large number of data points in a 3D coordinate system (i.e., x, y, and z) on the external surfaces of real-world objects (i.e., the limb) within the scan region to obtain the 3D point cloud. The 3D point cloud is therefore a representation of a scene or object in three dimensions. Point clouds are used in 3D modeling for various fields, such as, for example, manufacturing, imaging, architecture, 3D printing, 3D gaming, and virtual reality applications. After the 3D point cloud image is obtained, the process proceeds to block 308, where the process ends.

Figure 3A:
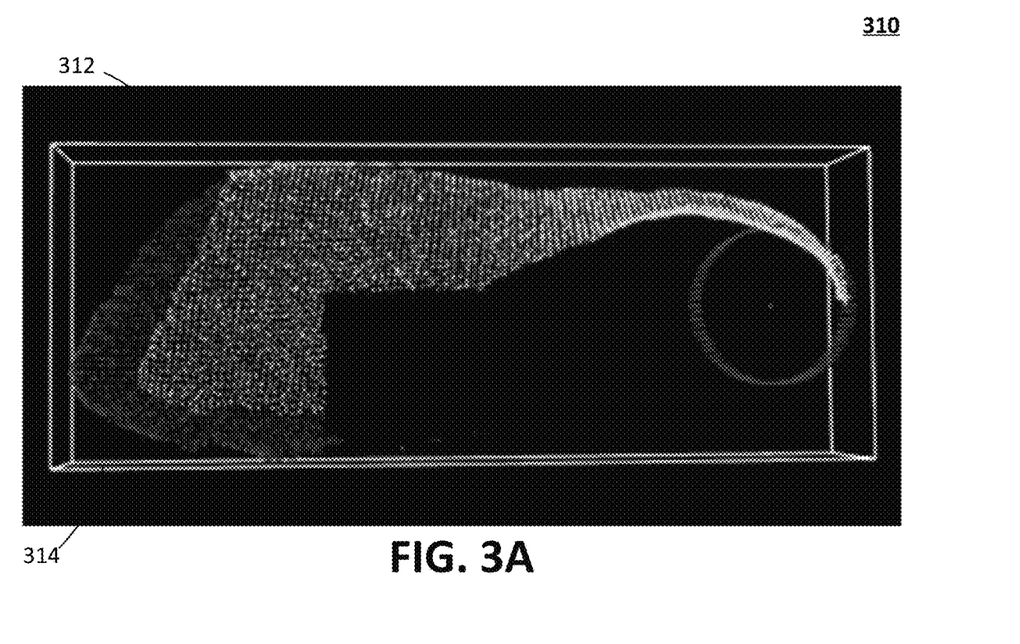
FIG. 3A is a visualization of a composited point cloud image for one (1) time interval according to an embodiment.

FIG. 3A is a visualization of a composited point cloud image 310 for one time interval according to an embodiment. In this instance, the 3D point cloud is a collection of data points on the external surfaces of a limb 312 in 3 dimensions for the person being measured. The limb 312, shown box fitted 314 inside of the point cloud image 310 of FIG. 3A, is a foot of the person being measured.

Returning to block 208 in FIG. 2, the process then proceeds to block 210.

In block 210, the captured limb is box fitted and identified. FIG. 4 is a flow diagram of an example method 400 of box fitting a limb within a 3D point cloud image according to an embodiment. The method 400 may generally be implemented in a system such as, for example, the limb measurement system 100 as shown in FIG. 1. More particularly, the method 400 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, and fixed-functionality logic hardware using circuit technology such as, for example, ASIC, CMOS or TTL technology, or any combination thereof.

The process begins in block 402 where the process immediately proceeds to decision block 404. In decision block 404, it is determined if an object within the point cloud image is recognized as being a limb. As indicated above, the classifier has been trained to recognize limbs within point clouds generated from the 3D cameras. Thus, the classifier determines if the point cloud image obtained in block 208 includes a limb. If the classifier does not recognize the object in the point cloud image as a limb, the process returns to block 208 to capture another 3D point cloud. If the classifier recognizes the object in the point cloud image as a limb, the process proceeds to block 406.

In block 406, a bounding box (or box fitting) approach is applied to the image of the limb within the 3D point cloud. In other words, a bounding box is placed around the limb. Based upon the recognition of the limb by the classifier, the classifier may know how many boxes are needed to fit the limb as well as the relative location of each box. The bounding box approach places a best fit bounding box around the limb within the 3D point cloud. A "best fit" bounding box is a rectangle with the smallest area that completely encompasses the limb or a subsection of the limb. Therefore, rectangular bounding box(es) are fitted to the object in the point cloud using a best fit bounding box algorithm. In some instances, the limb may include subsections. In such instances, a bounding box is placed around each subsection of the limb. Bounding boxes are used to enclose sections or subsections of the limb for identifying the limb and to obtain measurements (length, width, height) of the limb by measuring the bounded boxes. For example, if the limb is classified as a foot, only one bounding box may be needed (as shown with respect to FIG. 3A) to capture the foot. In another example, if the limb is classified as an arm, and the arm includes a lower portion and an upper portion of the arm, two bounding boxes may be needed, one for the upper arm and one for the lower arm (see FIG. 4A, discussed below). The process then proceeds to block 408.

Figure 3B:
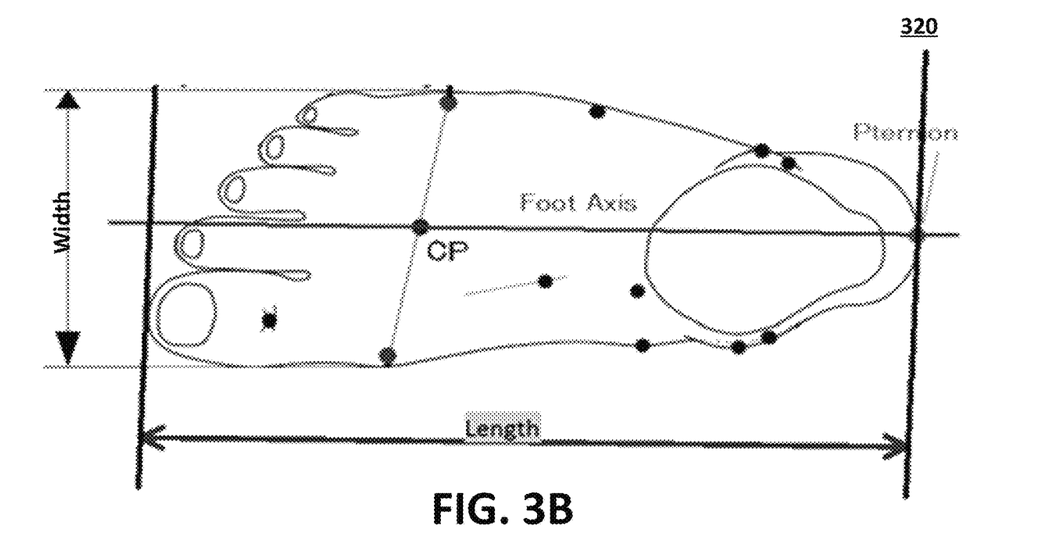
FIG. 3B illustrates a measurement process for the classified limb within the point cloud of FIG. 3A according to an embodiment.

In block 408, the dimensions of each box are obtained and recorded. The length, width, and height of each box are measured. FIG. 3B illustrates a measurement process for the limb within the point cloud of FIG. 3A. As previously indicated, the limb within the point cloud of FIG. 3A is a foot. FIG. 3B shows the length and width of the foot as measured from the bounded rectangular box shown in FIG. 3A.

Figure 4A:
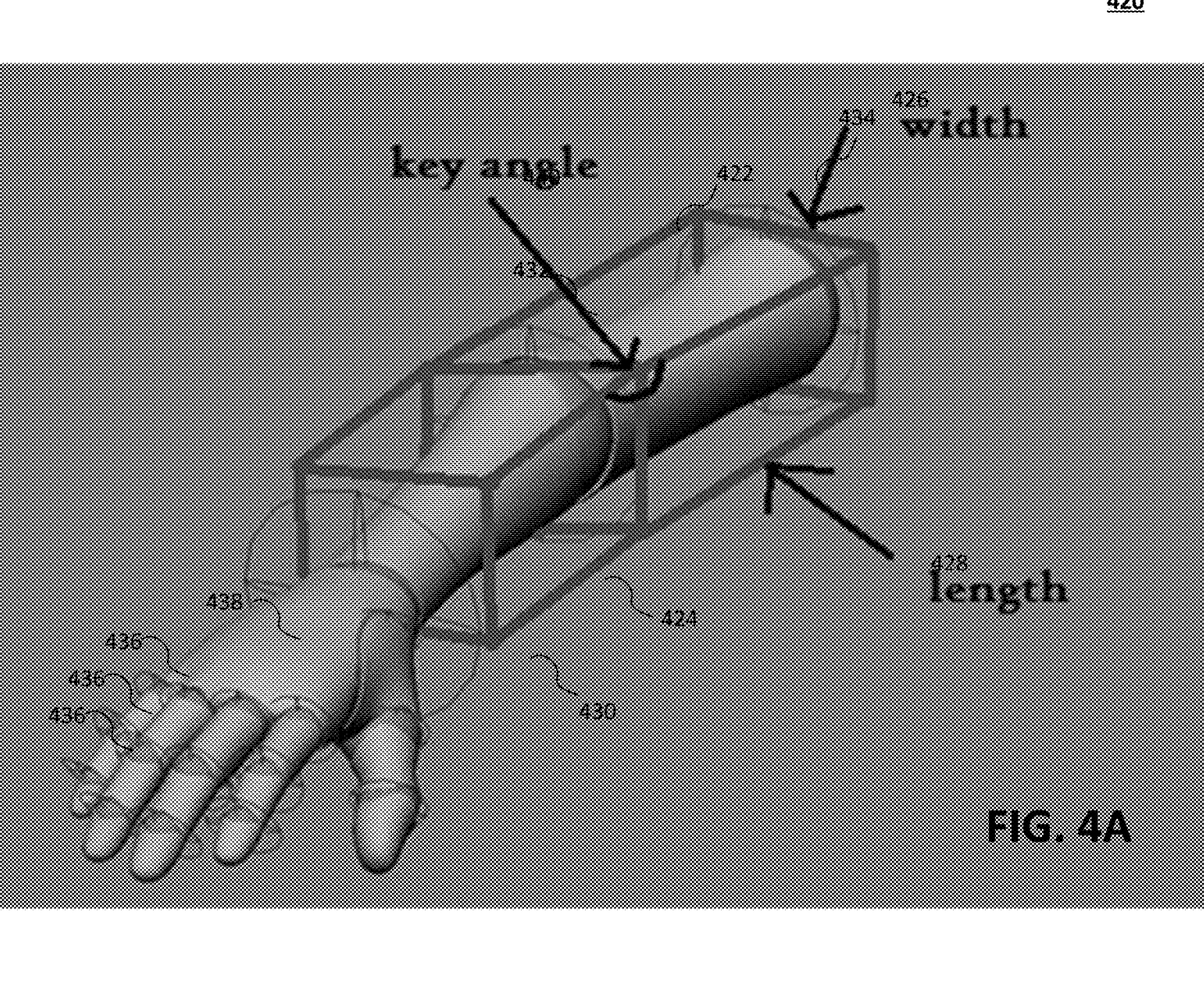
FIG. 4A illustrates measuring subsections of a limb using the bounded box fitting approach according to an embodiment.

If the limb within the point cloud is a limb having subsections that are box fitted, angles between the subsections are also measured and recorded. FIG. 4A illustrates measuring subsections of a limb using the bounded box fitting approach according to an embodiment. The limb 420 is an arm. The limb includes circles representative of joints and rectangles representative of subsections of the limb. For example, circles are shown at the wrist 430, elbow 432, top of the arm 434, and at the joints 436 of the fingers and thumb (shown on the pinky finger only) of the hand 438. Rectangular boxes 422 and 24 are fitted around the upper arm and the lower arm, respectively, which are attached at the elbow joint. When the elbow joint is bent, a key angle 440 is formed. Angles may be measured between planes created from the midpoints of the rectangular boxes as shown in FIG. 4A. Width, length, and height are measured using the bounded box dimensions. The process then proceeds to block 410.

As previously indicated, each portion of a limb has a geometry. Training the classifier on the different rectangular bounded box sizes for each limb type enables the classifier to better determine the identification of the limb in question based on the size of the rectangular box drawn around the limb. For example, returning back to FIG. 3A, the classifier may use the number of bounded boxes used and the length and width of the bounded box to make a determination that the dimensions more closely fit a foot. In another example, returning back to FIG. 4A, the classifier may use the number of bounded boxes used, the length and width of each of the bounded boxes, and the angle measurement of the key angle to make determination that the dimensions more closely fit an arm that includes both the upper and lower portions of the arm.

In block 410, the classifier identifies the limb. The data used to identify the limb is then added to the training data set to enable the classifier to be more accurate. The process then proceeds to block 412 where the process ends.

Figure 5A:
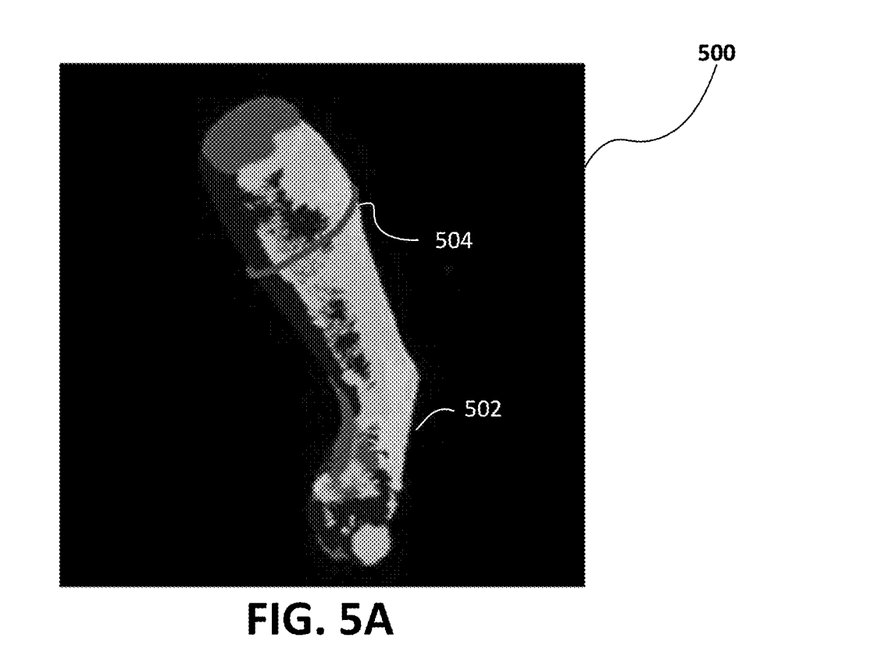
FIG. 5A illustrates a point cloud having the classification of a leg within the point cloud according to an embodiment.
Figure 5B:
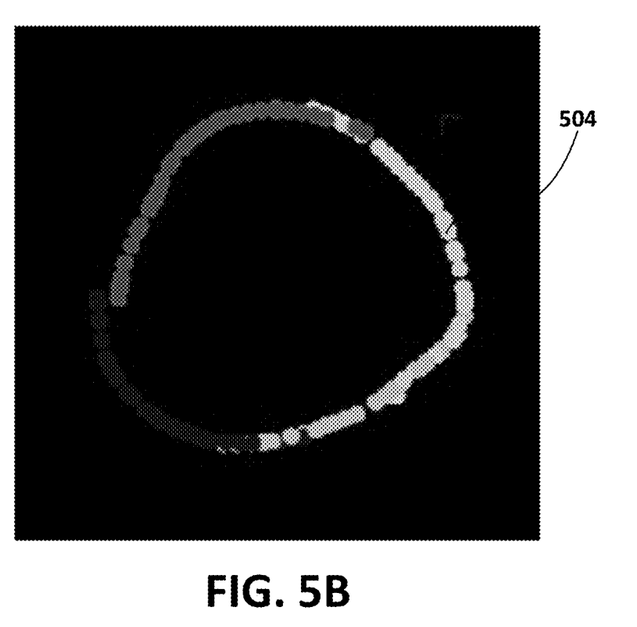
FIG. 5B illustrates a slice of the calf of the leg in 2D shown in FIG. 5A according to an embodiment.

Returning to block 210 of FIG. 2, after box fitting and measurements are obtained, the process proceeds to block 212. In block 212, slices of the boxes are created and the circumference of the 2D point cloud is measured from each slice. FIG. 5A illustrates a point cloud 500 having the classification of a leg and foot 502 within the point cloud 500. In this instance, the person may want to purchase a pair of boots, and that is why the person's leg and foot are captured in the 3D point cloud. Since everyone is different, the system must determine the thickest part of the person's calf to better fit the person with a pair of boots. To determine the thickest part, the circumference of each and every slice must be determined and compared against each other to find the portion of the calf that is the thickest. The location of the thickest slice is also an important factor in determining the best fitting boot for a customer. In FIG. 5A, the leg portion highlights a calf area 504 in which a single slice is generated. The slice 504 is representative of the maximum circumference of the leg. It identifies the widest point in the x-direction of the leg. Although not shown, a box around the leg portion of the limb would be sliced into many pieces to form a plurality of 2D point clouds. FIG. 5B illustrates the largest slice of the calf 504 as a 2D point cloud. The circumference of each slice of the limb is measured and recorded. The process proceeds to block 214.

Figures 6, 7:
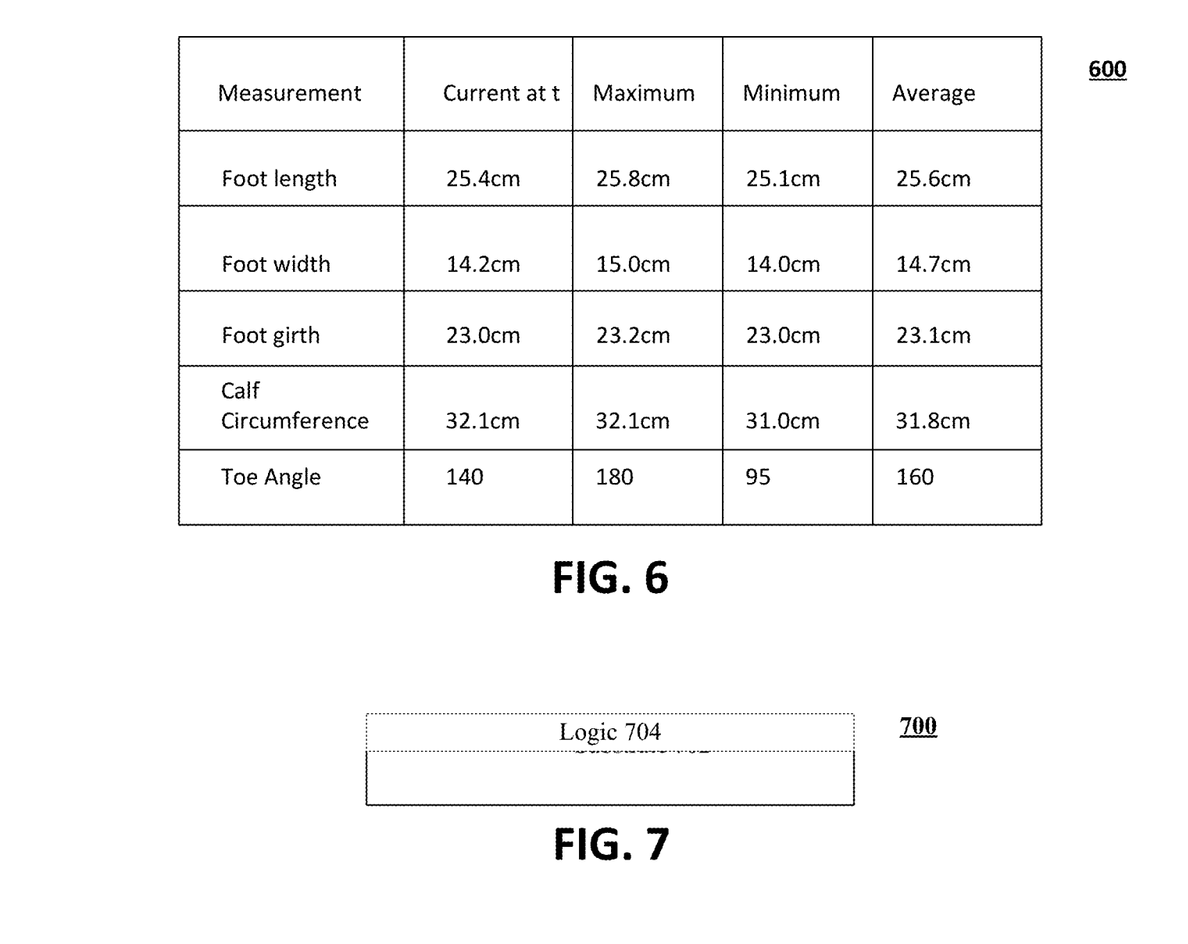
FIG. 6 shows an example table listing maximum, minimum, and average measurements for different limb attributes according to an embodiment.
FIG. 7 is an illustration of an example of a semiconductor package apparatus according to an embodiment.

In block 214, the current circumference measurement is compared against previous maximum and minimum measurements for the limb in question. If the current measurement is greater than the previous maximum or lower than the previous minimum, the corresponding previous maximum or previous minimum value is updated with the current measurement and an average value is computed. FIG. 6 shows an example table listing maximum, minimum, and average measurements for different limb attributes according to an embodiment. As previously indicated, the minimum and maximum measurements represent the range of motion parameters for the limb in question. The range of motion parameters may be different depending on the type of movements being made while capturing the 3D point cloud in block 208. Therefore, the type of activity being performed while wearing certain apparel must be taken into consideration. For instance, if the person is buying exercise apparel, capturing the person's limb while doing a more strenuous activity may be required. The process then proceeds to block 216.

In block 216, a counter t is incremented, enabling the process to move to the next frame of the depth camera video. In one embodiment, the counter acts as a clock that is recording data from the depth cameras over a period of time. The process then proceeds back to block 208 where another 3D point cloud is captured (with the limb in motion at a different time interval than the previous frame). This process continues until adequate minimum and maximum data is captured for the limb in question of the user. In one embodiment, this may be determined by an operator. In another embodiment, this may be determined when the minimum and maximum data for a limb of a user has been adequately reached for the type of apparel to be purchased. In this instance, no more data is needed and the process then proceeds to block 218.

In block 218, the samples are collected into a video stream that has 3-dimensional point cloud information. A simulation is run where the video stream and recorded axis and range of motion are input into the CNN that has been trained on previous data samples depicting a full range of rotation and motion. The sample is then enhanced to estimate the subject's full range of motion from the limited samples collected. In one embodiment, the simulation may be executed on the neuromorphic compute engine 106.

FIG. 7 shows a semiconductor package apparatus 700 (e.g., chip) that includes a substrate 702 (e.g., silicon, sapphire, gallium arsenide) and logic 704 (e.g., transistor array and other integrated circuit/IC components) coupled to the substrate 702. The logic 704, which may be implemented in configurable logic and/or fixed-functionality logic hardware, may generally implement one or more aspects of the methods 200, 300, and 400 (shown in FIG. 2, FIG. 3, and FIG. 4), already discussed.

Figure 8:
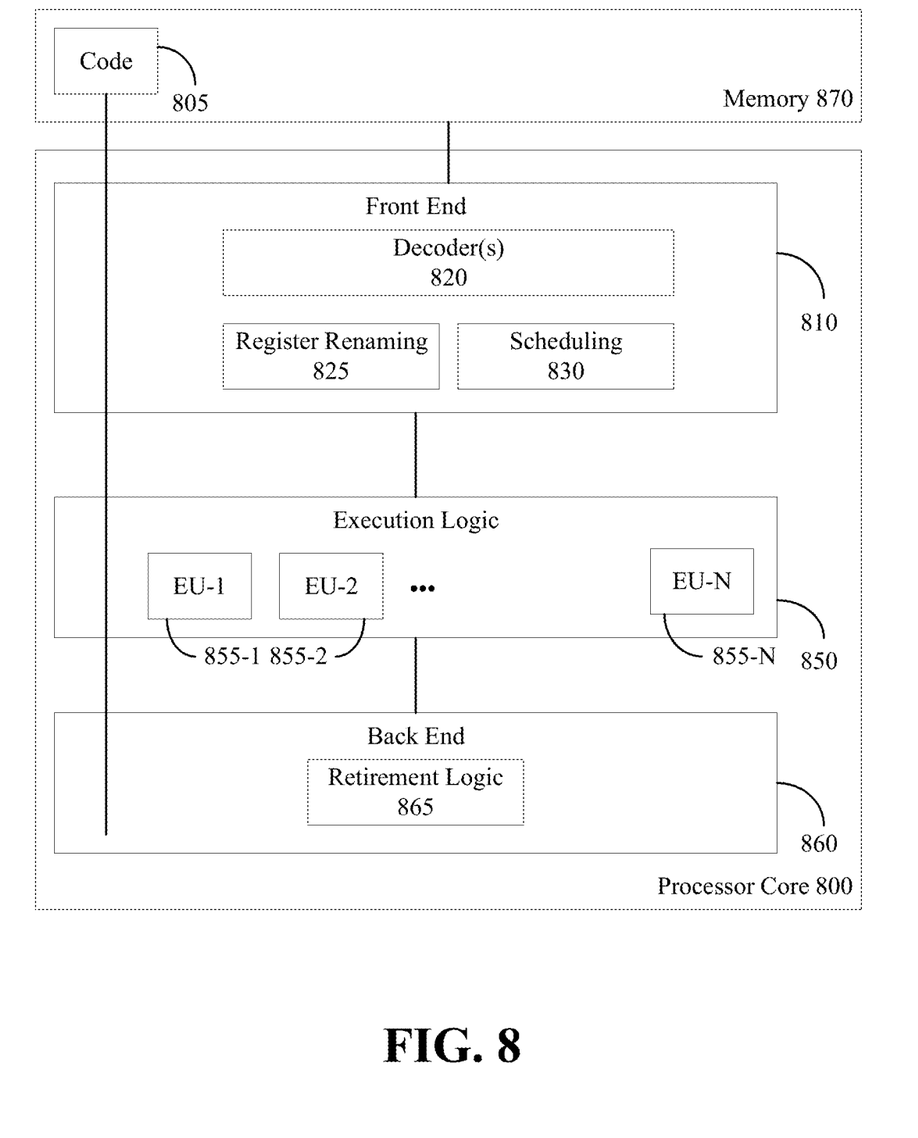
FIG. 8 is a block diagram of an exemplary processor according to an embodiment.

FIG. 8 illustrates a processor core 800 according to one embodiment. The processor core 800 may be the core for any type of processor, such as a micro-processor, an embedded processor, a digital signal processor (DSP), a network processor, or other device to execute code. Although only one processor core 800 is illustrated in FIG. 8, a processing element may alternatively include more than one of the processor core 800 illustrated in FIG. 8. The processor core 800 may be a single-threaded core or, for at least one embodiment, the processor core 800 may be multithreaded in that it may include more than one hardware thread context (or "logical processor") per core.

FIG. 8 also illustrates a memory 870 coupled to the processor core 800. The memory 870 may be any of a wide variety of memories (including various layers of memory hierarchy) as are known or otherwise available to those of skill in the art. The memory 870 may include one or more code 805 instruction(s) to be executed by the processor core 800, wherein the code 805 may implement the method 400 (FIG. 4), already discussed. The processor core 800 follows a program sequence of instructions indicated by the code 805. Each instruction may enter a front end portion 810 and be processed by one or more decoders 820. The decoder 820 may generate as its output a micro operation such as a fixed width micro operation in a predefined format, or may generate other instructions, microinstructions, or control signals which reflect the original code instruction. The illustrated front end portion 810 also includes register renaming logic 825 and scheduling logic 830, which generally allocate resources and queue the operation corresponding to the convert instruction for execution.

The processor core 800 is shown including execution logic 850 having a set of execution units 855-1 through 855-N. Some embodiments may include a number of execution units dedicated to specific functions or sets of functions. Other embodiments may include only one execution unit or one execution unit that can perform a particular function. The illustrated execution logic 850 performs the operations specified by code instructions.

After completion of execution of the operations specified by the code instructions, back end logic 860 retires the instructions of the code 805. In one embodiment, the processor core 800 allows out of order execution but requires in order retirement of instructions. Retirement logic 865 may take a variety of forms as known to those of skill in the art (e.g., re-order buffers or the like). In this manner, the processor core 800 is transformed during execution of the code 805, at least in terms of the output generated by the decoder, the hardware registers and tables utilized by the register renaming logic 825, and any registers (not shown) modified by the execution logic 850.

Although not illustrated in FIG. 8, a processing element may include other elements on chip with the processor core 800. For example, a processing element may include memory control logic along with the processor core 800. The processing element may include I/O control logic and/or may include I/O control logic integrated with memory control logic. The processing element may also include one or more caches.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the computing system within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A; B; C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

What is claimed is:

1. At least one non-transitory computer readable medium, comprising a set of instructions, which when executed by a computing device, cause the computing device to: initialize a scanning area; load a classifier trained to recognize limbs; capture, using at least one 3D camera, a frame representing a 3D point cloud including at least one limb of a person in motion; perform a box fitting algorithm on the captured at least one limb to enable the classifier to identify the at least one limb; and slice one or more boxes generated from the box fitting algorithm into a plurality of 2D point clouds to measure and record a circumference of each 2D point cloud to obtain limb range of motion parameters, wherein the limb range of motion parameters comprise a maximum and a minimum size of the at least one limb as a function of soft tissue expansion and contraction of the at least one limb while under pressure, force, and/or motion.

2. The at least one computer readable medium of claim 1, comprising further instructions, which when executed by the computing device, cause the computing device to capture additional frames of the 3D point cloud to obtain additional measurements, wherein if a current measurement exceeds a previous maximum size, the current measurement is updated as the maximum size, and wherein if the current measurement is less than a previous minimum size, the current measurement is updated as the minimum size.

3. The at least one computer readable medium of claim 2, comprising further instructions, which when executed by the computing device, cause the computing device to collect all measurements into a video stream having 3D point cloud information and simulate recorded motion through a neural network to estimate a full range of rotation and motion for the person.

4. The at least one computer readable medium of claim 3, wherein the full range of rotation and motion for the person enables manufacturing of apparel that comfortably fits the person while in motion.

5. The at least one computer readable medium of claim 1, wherein instructions to initialize a scanning area comprise instructions to calibrate an x, y, z scanning region relative to a floor and walls of the scanning area.

6. The at least one computer readable medium of claim 1, wherein the classifier is trained to recognize limbs within the 3D point clouds and to specify a number of bounding rectangular boxes needed to fit around the captured at least one limb.

7. The at least one computer readable medium of claim 1, wherein instructions to perform a box fitting algorithm comprises instructions to:
fit a bounded rectangular box around the captured at least one limb, wherein if the captured at least one limb includes subsections, fit bounded rectangular boxes around each of the subsections of the captured at least one limb;
measure and record each of the bounded rectangular boxes and any angles between the bounded rectangular boxes of limbs having subsections; and
based on dimensions of each of the bounded rectangular boxes, use the classifier to identify the at least one limb, wherein the classifier is trained to identify a type of limb within the 3D point cloud based on sizes of the bounded rectangular boxes used.

8. The at least one computer readable medium of claim 7, wherein instructions to fit a bounded rectangular box around the captured at least one limb comprises instructions to fit one or more best fit bounded rectangular boxes around the captured at least one limb, wherein a best fit bounded rectangular box comprises a rectangular box having a smallest area that completely contains the captured at least one limb or the subsection of the captured at least one limb.

9. A method for measuring limb range of motion comprising:
initializing a scanning area;
loading a classifier trained to recognize limbs;

capturing, using at least one 3D camera, a frame representing a 3D point cloud including at least one limb of a person in motion;

performing a box fitting algorithm on the captured at least one limb to enable the classifier to identify the at least one limb; and slicing one or more boxes generated from the box fitting algorithm into a plurality of 2D point clouds to measure and record a circumference of each 2D point cloud to obtain limb range of motion parameters, wherein the limb range of motion parameters comprise a maximum and a minimum size of the at least one limb as a function of soft tissue expansion and contraction of the at least one limb while under pressure, force, and/or motion.

10. The method of claim 9, further comprising capturing additional frames of the 3D point cloud to obtain additional measurements, wherein if a current measurement exceeds a previous maximum size, the current measurement is updated as the maximum size, and wherein if the current measurement is less than a previous minimum size, the current measurement is updated as the minimum size.

11. The method of claim 10, further comprising collecting all measurements into a video stream having 3D point cloud information and simulating recorded motion through a neural network to estimate a full range of rotation and motion for the person.

12. The method of claim 11, wherein the full range of rotation and motion for the person enables manufacturing of apparel that comfortably fits the person while in motion.

13. The method of claim 9, wherein initializing a scanning area comprises calibrating an x, y, z scanning region relative to a floor and walls of the scanning area.

14. The method of claim 9, wherein the classifier is trained to recognize limbs within the 3D point clouds and to specify a number of bounding rectangular boxes needed to fit around the captured at least one limb.

15. The method of claim 9, wherein performing a box fitting algorithm comprises:

fitting a bounded rectangular box around the captured at least one limb, wherein if the captured at least one limb includes subsections, fitting bounded rectangular boxes around each of the subsections of the captured at least one limb;

measuring and recording each of the bounded rectangular boxes and any angles between the bounded rectangular boxes of captured limbs having subsections; and based on dimensions of each of the bounded rectangular boxes, using the classifier to identify the captured at least one limb, wherein the classifier is trained to identify a type of limb within the 3D point cloud based on sizes of the bounded rectangular boxes used.

16. The method of claim 15, wherein fitting a bounded rectangular box around the captured at least one limb comprises fitting one or more best fit bounded rectangular boxes around the captured at least one limb, wherein a best fit bounded rectangular box comprises a rectangular box having a smallest area that completely contains the captured at least one limb or the subsection of the captured at least one limb.

17. A limb range of motion system comprising:

a measurement device having one or more depth cameras with a 360-degree view of a limb in motion; and a computer system coupled to the measurement device, the computer system having at least one processor coupled to the measurement device, the computer system including one or more memory devices coupled to the at least one processor, the one or more memory devices including instructions, which when executed by the at least one processor, cause the system to:

initialize a scanning area;

load a classifier trained to recognize limbs into memory;

capture a frame representing a 3D point cloud including at least one limb of a person in motion;

perform a box fitting algorithm on the captured at least one limb to enable the classifier to identify the at least one limb; and slice one or more boxes generated from the box fitting algorithm into a plurality of 2D point clouds to measure and record a circumference of each 2D point cloud to obtain limb range of motion parameters.

18. The system of claim 17, wherein the limb range of motion parameters comprise a maximum and a minimum size of the at least one limb as a function of soft tissue expansion and contraction of the at least one limb while under pressure, force, and/or motion.

19. The system of claim 17, wherein the instructions, when executed, further cause the system to capture additional frames of the 3D point cloud to obtain additional measurements, wherein if a current measurement exceeds a previous maximum size, the current measurement is updated as the maximum size, and wherein if the current measurement is less than a previous minimum size, the current measurement is updated as the minimum size.

20. The system of claim 19, comprising further instructions, which when executed, cause the system to collect all measurements into a video stream having 3D point cloud information and simulate recorded motion through a neural network to estimate a full range of rotation and motion for the person.

21. The system of claim 20, wherein the full range of rotation and motion for the person enables manufacturing of apparel that comfortably fits the person while in motion.

22. The system of claim 17, wherein instructions to initialize a scanning area comprise instructions to calibrate an x, y, z scanning region relative to a floor and walls of the scanning area.

23. The system of claim 17, wherein the classifier is trained to recognize limbs within the 3D point clouds and to specify a number of bounding rectangular boxes needed to fit around the captured at least one limb.

24. The system of claim 17, wherein instructions to perform a box fitting algorithm comprises instructions to:

fit a bounded rectangular box around the captured at least one limb, wherein if the captured at least one limb includes subsections, fit bounded rectangular boxes around each of the subsections of the captured at least one limb;

measure and record each of the bounded rectangular boxes and any angles between the bounded rectangular boxes of limbs having subsections; and based on dimensions of each of the bounded rectangular boxes, use the classifier to identify the at least one limb, wherein the classifier is trained to identify a type of limb within the 3D point cloud based on sizes of the bounded rectangular boxes used.

25. The system of claim 24, wherein instructions to fit a bounded rectangular box around the captured at least one limb comprises instructions to fit one or more best fit bounded rectangular boxes around the captured at least one limb, wherein a best fit bounded rectangular box comprises a rectangular box having a smallest area that completely contains the captured at least one limb or the subsection of the captured at least one limb.

* * * * *